(12) United States Patent
Grabowski et al.

(10) Patent No.: US 10,016,247 B2
(45) Date of Patent: *Jul. 10, 2018

(54) PACKAGING FOR MEDICAL DEVICES

(71) Applicant: DePuy Synthes Products, Inc., Raynham, MA (US)

(72) Inventors: Woitech Grabowski, Solothurn (CH); Werner Schweiker, Solothurn (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/629,376

(22) Filed: Jun. 21, 2017

(65) Prior Publication Data

US 2017/0281292 A1    Oct. 5, 2017

Related U.S. Application Data

(63) Continuation of application No. 14/236,271, filed as application No. PCT/US2012/043988 on Jun. 25, 2012, now Pat. No. 9,707,039.

(60) Provisional application No. 61/515,643, filed on Aug. 5, 2011.

(51) Int. Cl.
| | |
|---|---|
| *A61B 17/06* | (2006.01) |
| *A61B 50/31* | (2016.01) |
| *B65D 73/00* | (2006.01) |
| *A61B 50/30* | (2016.01) |

(52) U.S. Cl.
CPC ............ *A61B 50/31* (2016.02); *A61B 50/30* (2016.02); *B65D 73/0092* (2013.01); *A61B 2050/3015* (2016.02); *A61B 2050/314* (2016.02)

(58) Field of Classification Search
CPC ...................... B65D 73/0092; B65D 73/0085; A61B 50/30; A61B 19/026; A61B 2050/3015; A61B 2050/314
USPC ......... 206/363, 438–441; 229/240, 242–244, 229/307, 313, 314, 316
See application file for complete search history.

(56) References Cited

U.S. PATENT DOCUMENTS

| | | | |
|---|---|---|---|
| 2,476,740 A | 7/1949 | Krall | |
| 2,828,065 A * | 3/1958 | Heywood | .............. B65D 27/34 206/459.5 |
| 3,301,392 A | 1/1967 | Regan, Jr. | |

(Continued)

FOREIGN PATENT DOCUMENTS

| | | |
|---|---|---|
| CN | 1327425 | 12/2001 |
| CN | 1712323 | 12/2005 |

(Continued)

*Primary Examiner* — Luan K Bui
(74) *Attorney, Agent, or Firm* — Fay Kaplun & Marcin, LLP

(57) ABSTRACT

An envelope for housing a medical device includes a body including first and second panels connected to one another along an edge thereof to define an interior space sized and shaped to house a medical device sealed within a packet and a first opening arrangement including a perforation extending about the body along the first and second panels to define a break portion breakable from a remaining portion of the body to open the envelope along with a second opening arrangement including a tab extending from a portion of the body such that pulling the tab in a direction away from the body tears a portion of the perforation extending along the first panel to open the envelope.

11 Claims, 10 Drawing Sheets

(56) References Cited

U.S. PATENT DOCUMENTS

| | | | |
|---|---|---|---|
| 3,301,395 A * | 1/1967 | Swezey | B65D 73/0092 |
| | | | 206/462 |
| 3,334,804 A * | 8/1967 | Watts, Jr. | B65D 75/28 |
| | | | 206/463 |
| 3,428,171 A | 2/1969 | Blish | |
| 3,595,446 A * | 7/1971 | Hellstrom | B65D 47/2031 |
| | | | 206/540 |
| 3,941,307 A | 3/1976 | Van Malderghem | |
| 4,106,621 A | 8/1978 | Sorenson | |
| 4,116,338 A | 9/1978 | Weichselbaum | |
| 4,166,539 A | 9/1979 | Allen et al. | |
| 4,194,622 A | 3/1980 | Lewis | |
| 4,310,117 A | 1/1982 | Gullett | |
| 4,435,001 A | 3/1984 | Mills et al. | |
| 4,470,511 A | 9/1984 | Meeker et al. | |
| 4,492,308 A | 1/1985 | Meeker et al. | |
| 4,607,749 A * | 8/1986 | Jacob | B65D 27/16 |
| | | | 229/313 |
| 4,729,507 A * | 3/1988 | Kim | B65D 27/38 |
| | | | 229/301 |
| 4,747,535 A | 5/1988 | Haase et al. | |
| 4,765,485 A | 8/1988 | Perkins | |
| 4,819,807 A | 4/1989 | Giger | |
| 4,877,139 A | 10/1989 | Kim | |
| 4,896,821 A | 1/1990 | Bell | |
| 4,934,536 A | 6/1990 | Mills | |
| 5,069,384 A | 12/1991 | Bell | |
| 5,076,431 A | 12/1991 | Thompson | |
| 5,133,496 A | 7/1992 | Davidson | |
| 5,439,102 A | 8/1995 | Brown et al. | |
| 5,467,917 A | 11/1995 | Potter | |
| 5,503,328 A | 4/1996 | Roccaforte et al. | |
| 5,579,910 A * | 12/1996 | Bennett | B65D 75/366 |
| | | | 206/362 |
| 5,791,556 A | 8/1998 | Hawkins | |
| 5,947,288 A | 9/1999 | Dykstra et al. | |
| 6,006,985 A | 12/1999 | Hawkins | |
| 6,010,000 A | 1/2000 | Tran | |
| 6,457,638 B1 | 10/2002 | Schmidt | |
| 6,457,863 B1 * | 10/2002 | Vassallo | B65D 33/007 |
| | | | 150/129 |
| 6,491,213 B2 | 12/2002 | Purcell | |
| 6,588,653 B1 | 7/2003 | Schmidt | |
| 6,662,995 B1 | 12/2003 | Mori | |
| 6,716,150 B2 | 4/2004 | Purcell | |
| 7,178,713 B2 | 2/2007 | Stude | |
| 7,475,781 B2 | 1/2009 | Kobayashi et al. | |
| 8,490,794 B2 | 7/2013 | Kalin | |
| 2002/0130169 A1 | 9/2002 | Purcell | |
| 2003/0015581 A1 | 1/2003 | Purcell | |
| 2003/0173397 A1 | 8/2003 | Kourakov | |
| 2003/0183643 A1 | 10/2003 | Fagen et al. | |
| 2004/0140346 A1 | 7/2004 | Tay | |
| 2004/0217156 A1 | 11/2004 | Purcell | |
| 2005/0226542 A1 | 10/2005 | Kendall et al. | |
| 2006/0124708 A1 | 6/2006 | Lo Duca | |
| 2006/0266808 A1 | 11/2006 | DeLa Vergne | |
| 2006/0278687 A1 | 12/2006 | Sexton | |
| 2007/0023309 A1 | 2/2007 | Davis | |
| 2007/0023492 A1 | 2/2007 | Stude | |
| 2008/0223914 A1 | 9/2008 | Choi | |
| 2009/0101697 A1 | 4/2009 | Yost et al. | |
| 2010/0096283 A1 | 4/2010 | Wiesinger | |

FOREIGN PATENT DOCUMENTS

| | | |
|---|---|---|
| CN | 2757759 | 2/2006 |
| CN | 1923630 | 3/2007 |
| CN | 201350989 | 11/2009 |
| CN | 201400345 | 2/2010 |
| EP | 1834568 | 9/2007 |
| FR | 2897597 | 8/2007 |
| JP | 62-017537 | 2/1987 |
| JP | 02-102353 | 8/1990 |
| JP | 7-9326 | 2/1995 |
| JP | 2005-075430 | 3/2005 |
| JP | 2008-150112 | 7/2008 |
| WO | 96/20882 | 7/1996 |
| WO | 2009/099852 | 8/2009 |

* cited by examiner

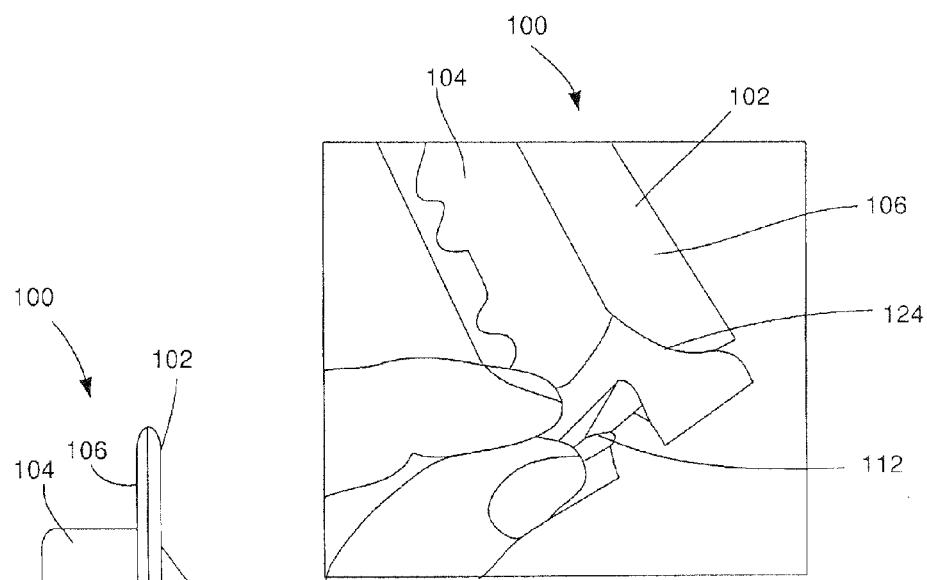
Fig. 4
Fig. 3
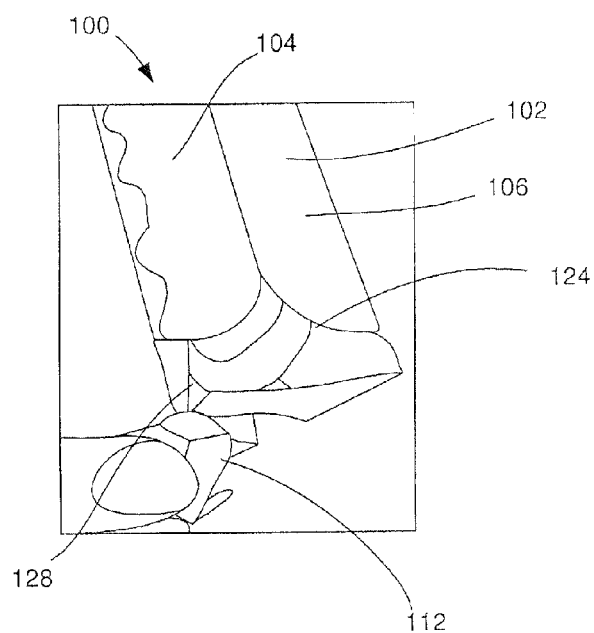
Fig. 5

US 10,016,247 B2

PACKAGING FOR MEDICAL DEVICES

PRIORITY CLAIM

The present application is a Continuation Application of U.S. patent application Ser. No. 14/236,271 filed on Mar. 31, 2014, now U.S. Pat. No. 9,707,039; which is a 371 of PCT Appln. Ser. No. PCT/US2012/43988 filed on Jun. 25, 2012; which claims priority to U.S. Provisional Patent Application Ser. No. 61/515,643 filed on Aug. 5, 2011. The entire disclosures of this patent(s)/application(s) are expressly incorporated herein by reference.

BACKGROUND

Medical devices must be packaged and sealed such that the devices remain sterile until ready for use. Current packages for medical devices include a tear off portion extending along an edge thereof. However, these tear off portions may be difficult to locate and utilize. Even when the tear off portions are easily identifiable, opening of the packages via the tear off portions may be difficult due to interference thereof by the contents of the packages.

SUMMARY OF THE INVENTION

The present invention is directed to an envelope for housing a medical device comprising a body including first and second panels connected to one another along an edge thereof to define an interior space sized and shaped to house a medical device sealed within a packet and a first opening arrangement including a perforation extending about the body along the first and second panels to define a break portion breakable from a remaining portion of the body to open the envelope along with a second opening arrangement including a tab extending from a portion of the body such that pulling the tab in a direction away from the body tears a portion of the perforation extending along the first panel to open the envelope.

BRIEF DESCRIPTION OF THE DRAWINGS

FIG. 3 shows a side view of the package according to FIG. 1;

FIG. 4 shows a perspective view of a pull tab of the package of FIG. 1 being grasped by a user;

FIG. 5 shows a perspective view of the package of FIG. 1 being opened via the pull-away tab;

DETAILED DESCRIPTION

The present invention may be further understood with reference to the following description and the appended drawings, wherein like elements are referred to with the same reference elements. The present invention relates to packaging and, in particular, relates to packaging for medical devices. An exemplary embodiment of the present invention is directed to an envelope configured to house a medical device sealed within a packet and including two opening arrangements, a tear off tab and a break portion, which are easily identifiable by a user and permit a user to choose which opening arrangement to utilize.

Figure 1:
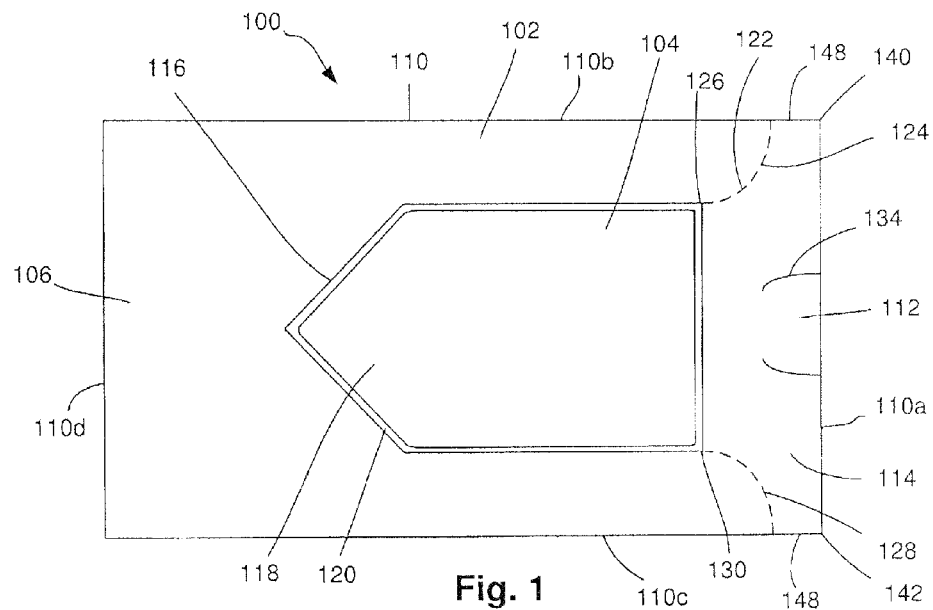
FIG. 1 shows a top plan view of a package according to an exemplary embodiment of the present invention.
Figure 2:
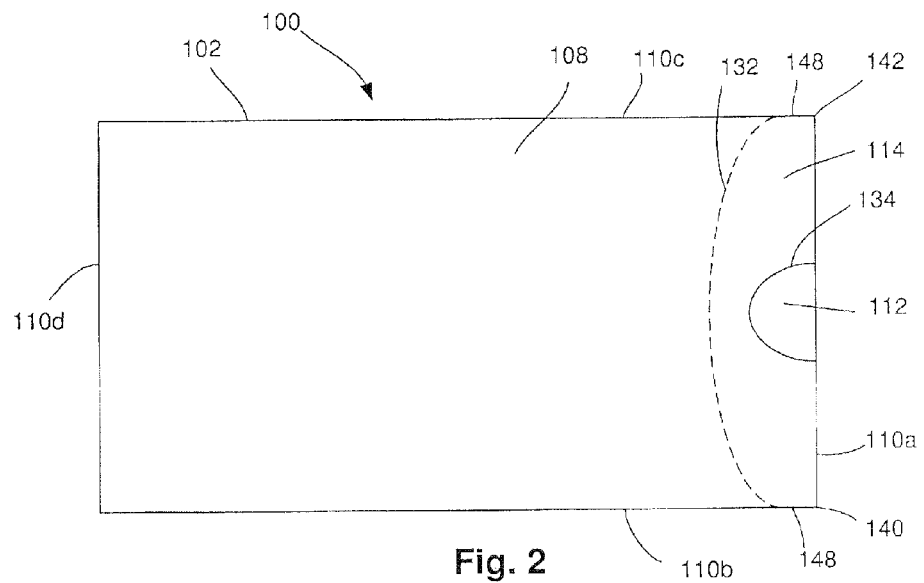
FIG. 2 shows a bottom plan view of the package according to FIG. 1.
Figure 6:
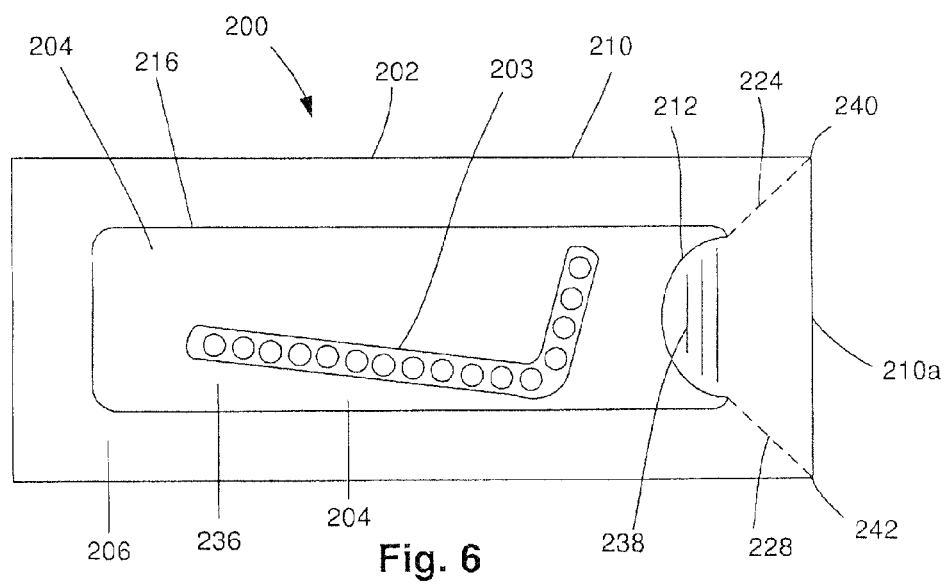
FIG. 6 shows a top plan view of a package according to another exemplary embodiment of the present invention.
Figure 7:
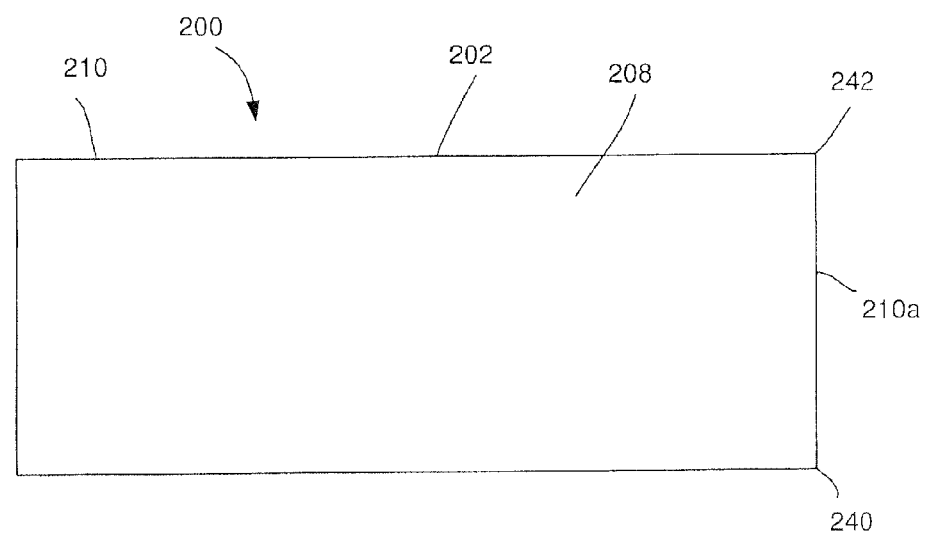
FIG. 7 shows a bottom plan view of the package of FIG. 6.

As shown in FIGS. 1-3, a package 100 according to an exemplary embodiment of the present invention comprises an envelope 102 sized and shaped to house a medical device such as, for example, bone plates and/or bone fixation elements, which may be sealed in a packet 104 such that the device remains sterile prior to use. The envelope 102 may be formed of substantially planar, equally sized and shaped first and second panels 106, 108 which are connected to one another along an edge 110 thereof. The envelope 102 may also include a window 116 extending through the first panel 106 such that the packet 104 and the contents thereof are visible therethrough. The envelope 102 may be opened via a pull tab 112 extending over the edge 110 or a break-off portion 114 extending along a portion of the edge 110. Thus, a user may choose whether to utilize the pull tab 112 or the break-off portion 114 when opening the envelope 102 to access the packet 104 and the device sealed therein. It will be understood by those of skill in the art that the envelope 102 facilitates shipment and storage of the device sealed within the packet 104, and may include information identifying the device thereon.

In an exemplary embodiment, the envelope 102 may be substantially rectangular such that rectangular first and second panels 106, 108 are connected via four substantially straight edges 110a, 110b, 110c, 110d extending thereabout. In one exemplary embodiment, the envelope 102 may be connected and closed along each of the edges 110a-110d. In another exemplary embodiment, the first and second panels 106, 108 may be connected along three of the edges 110a, 110b, 110c such that the fourth edge 110d is open. The open fourth edge 110d may be sealed via a product sticker or label which identifies the device housed therein. It will be understood by those of skill in the art, however, that the envelope 102 may have any of a variety of shapes and sizes so long as an interior space defined by the first and second panels 106, 108 is sized and shaped to accommodate the sealed packet 104 therein.

The packet 104 may be formed of a transparent material such that the device sealed therewithin is visible therethrough. The packet 104 may be, for example, a substantially flat, sealed pouch (not shown) which may be entirely housed within the envelope 102. In another example, the packet 104 may be a sealed tray including a tray portion 118 and a rim portion 120 extending thereabout such that the rim portion 120 is housed within the interior space of the envelope 102 while the tray portion 118 extends from the interior space through the window 116 to an exterior of the envelope 102.

The first panel 106 of the envelope 102 includes the window 116, which may be sized and shaped such that at least a portion of the device housed therein is visible therethrough. In an exemplary embodiment in which the sealed packet 104 is a pouch, the window 116 may include a transparent film extending across the window 116 to cover the window 116 while also permitting the contents of the envelope 102 and/or the packet 104 to be visible therethrough. In another exemplary embodiment in which the packet 104 is a tray, the window 116 may be sized and shaped to accommodate the tray portion 118 therethrough. For example, the window 116 may be a polygonal shape which corresponds to the size and shape of the tray portion 118.

The envelope 102 includes a perforation 122 extending thereabout proximate a portion of the edge 110 to define the break portion 114. In an exemplary embodiment in which the envelope 102 is substantially rectangular, the perforation 122 extends about the envelope 102 proximate the first edge 110a. The perforation 122 includes a first portion 124 extending along the first panel 106 from a first corner 126 of the window 116 to the second edge 110b adjacent the first edge 110a and a second portion 128 extending along the first panel 106 from a second corner 130 of the window 116 to the third edge 110c, also adjacent to the first edge 110a. A third portion 132 of the perforation 122 extends along the second panel 108 to connect the first portion 124 to the second portion 128. Thus, a user may grip and break the break portion 114 from a remaining portion of the envelope 102 via the entire length of the perforation 122, to open the envelope 102 and access the packet 104 housed therein.

A user may also open the envelope 102 via the pull tab 112. The tab 112 may be defined by a cut 134 extending along the break portion 114 of the envelope 102. The cut 134 extends from the first panel 106 and over the first edge 110a to the second panel 108 such that the tab 112 may be lifted away from the second panel 108 while remaining attached to the first panel 106. Thus, the envelope 102 may be opened by grasping the tab 112, as shown in FIG. 4, and pulling the tab 112 away from the envelope 102, as shown in FIG. 5, such that the envelope 102 tears along the first and second portions 124, 128 of the perforation 122. The envelope 102 may further include slits 148 extending from the perforation 122 along the second and third edges 110b, 110c to corners 140, 142 of the first edge 110a so that when the tab 112 is pulled to open the envelope 102, a clean opening is formed near the edge 110a to facilitate easy removal of the packet 104 therefrom. The tab 112 may also include printed text therealong, which identifies the tab 112.

The envelope 102 may be constructed from a single piece of cardboard or heavy paper stock material which is sized and shaped such that, when folded, the envelope 102 is configured as described above. The material may be manufactured to include the window 116 and the perforation 122 formed therealong so that the material may be folded along edges 110a, 110b, 110c, 110d to define the first and second panels 106, 108. Thus, the packet 104 may be easily packed within the envelope 102 by placing the packet 104 along a portion of the material corresponding to the first panel 106 and folding remaining segments of the material thereover. Adhesive may be applied to overlapping segments of the material to close the envelope 102 and hold the packet 104 therein.

It will be understood by those of skill in the art that a package according to the present invention may also utilize one the two opening arrangements described above. For example, as shown in FIGS. 6-9, a package 200 according to another exemplary embodiment of the present invention may be substantially similar to the package 100 described above, comprising an envelope 202 which houses a device 203 sealed within a packet 204. The envelope 202, however, only includes a pull tab 212 for opening the envelope 202.

Similarly to the envelope 102, the envelope 202 may be formed of substantially planar first and second panels 206, 208 connected to one another along an edge 210. The envelope 202 also includes a window 216 formed through the first panel 206 so that the packet 204 and/or the device 203 is visible therethrough. The envelope 202 may also include a transparent film 236 extending across the window 216 such that the window 216 is covered while also permitting the contents of the envelope 202 to be visible therethrough. The packet 204 may be, for example, a substantially flat, transparent pouch, which seals the device 203 therein so that the device 203 is also visible therethrough.

Figure 8:
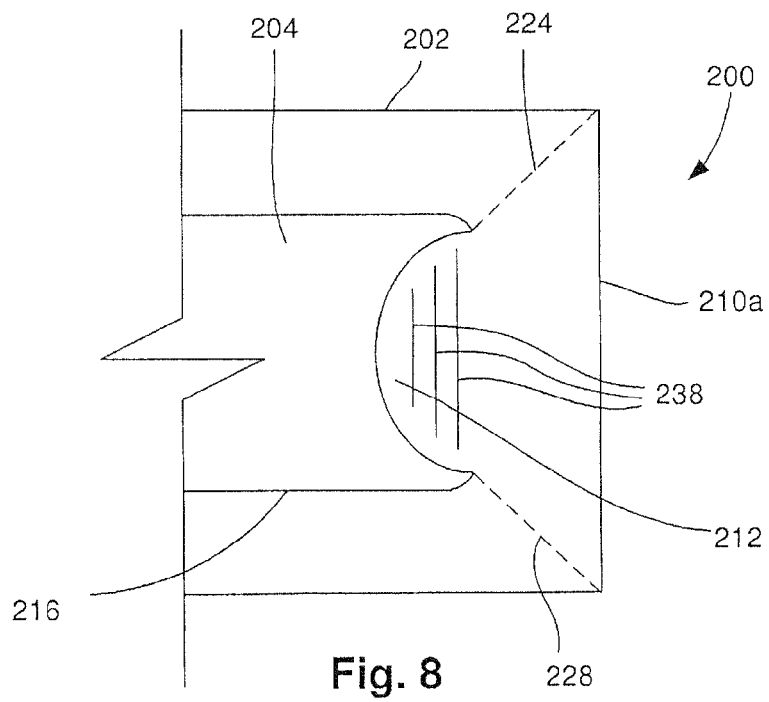
FIG. 8 shows an enlarged top plan view of a portion of the package of FIG. 6, in a closed configuration.

As shown in FIG. 8, the tab 212 extends from the first panel 206 over a portion of the window 216 so that the tab 212 is easily identifiable by a user. The tab 212 may include a plurality of grooves 238 extending therealong such that the tab 212 is flexible and may be easily gripped by the user. The envelope 202 further includes a first perforation 224 extending along the first panel 206 from a first side of the tab 212 toward the edge 210 and a second perforation 228 extending along the first panel 206 from a second side of the tab 212 toward the edge 210 such that when the user grips and pulls the tab 212, the first panel 206 tears along the first and second perforations 224, 228 to open the envelope 202. In an exemplary embodiment in which the envelope 202 is rectangular, the first and second perforations 224, 228 may extend toward a first edge 210a so that pulling the tab 212 toward the first edge 210a opens the envelope 202 along the first edge 210a. In a further exemplary embodiment, the first and second perforations 224, 228 may extend toward corners 240, 242, which form ends of the first edge 210a. It will be understood by those of skill in the art that the first and second perforations 224, 228 may extend along the first panel 206 in a variety of configurations so long as pulling the tab 212 tears the first and second perforations 224, 228 to open the envelope 202. Where the perforations 224, 228 do not extend to the corners 240, 242, the envelope 202 may also include slits extending along the first edge 210a from the first and second perforations 224, 228 toward the corners 240, 242 to ensure a clean opening and easy removal of the packet 204 therefrom.

Figure 9:
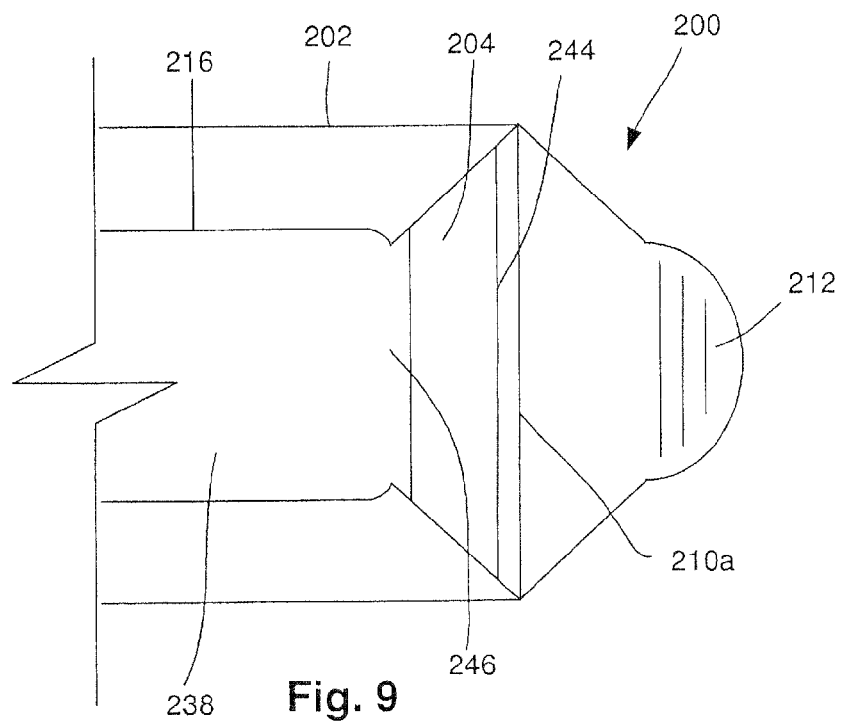
FIG. 9 shows an enlarged top plan view of a portion of the package of FIG. 6, in an open configuration.

Once the tab 212 has been pulled and the first and second perforations 224, 228 are torn, as shown in FIG. 9, an opening is formed at the first edge 210a such that an end 244 of the packet 204 may be grasped and pulled from the envelope 202. The end 244 may extend beyond an end 246 of the transparent film 238 covering the window 214, between the first end 246 of the film 238 and the first edge 210a, to facilitate easy grasping and pulling of the end 244 of the packet 204.

Figure 10:
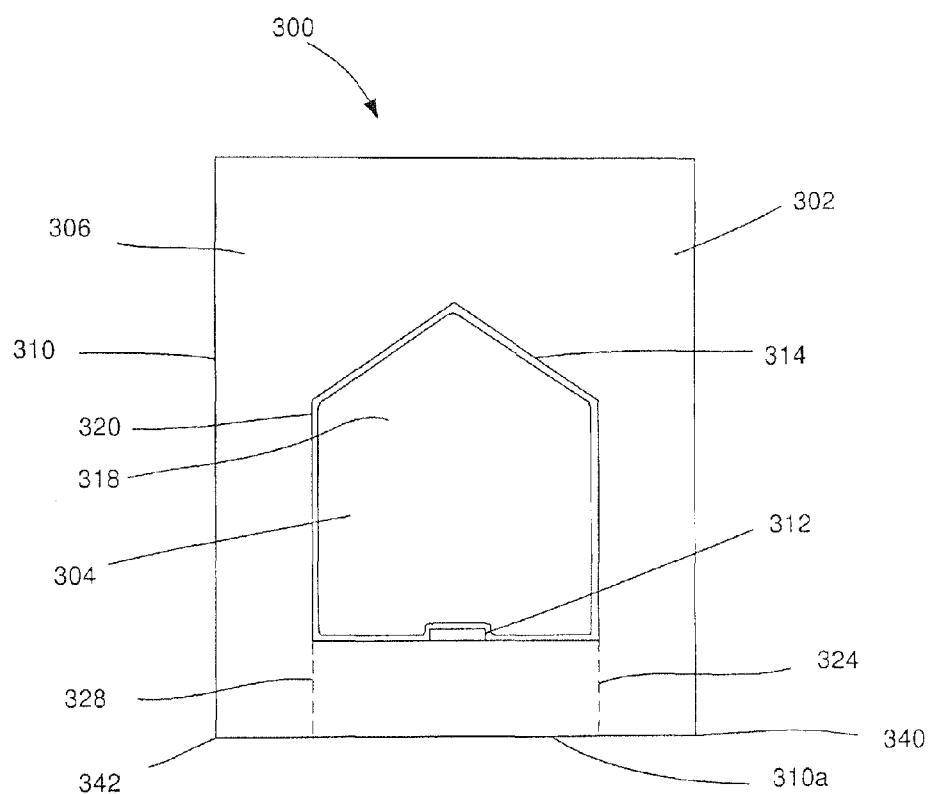
FIG. 10 shows a top plan view of a package according to yet another exemplary embodiment of the present invention.
Figure 11:
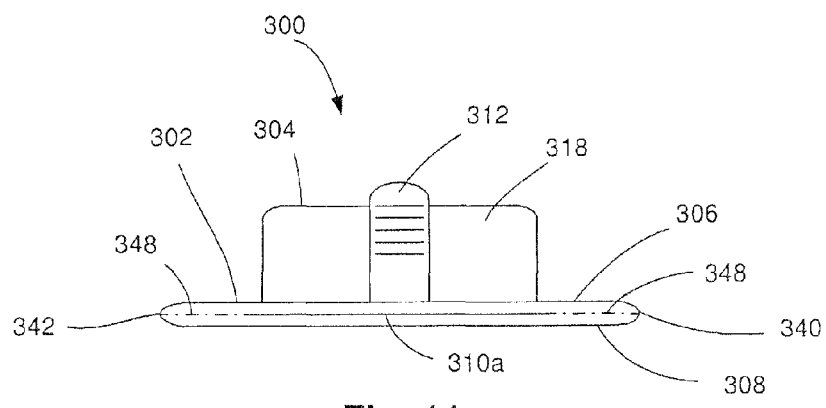
FIG. 11 shows a side view of the package of FIG. 10.

As shown in FIG. 10-11, a package 300 according to another exemplary embodiment of the present invention may be substantially similar to the packages 100, 200 comprising an envelope 302 which may be opened via a pull tab 312 to access a sealed packet 304 housed therein.

Similarly to the envelope 202, the envelope 302 is formed of two substantially planar panels 306, 308 connected to one another along an edge 310 thereof. The packet 304 may be substantially similar to the tray described above in regard to the packet 104, including a tray portion 318 and a rim 320 extending thereabout such that the rim 320 is housed within an interior space of the envelope 302 while the tray portion 318 extends from the interior space through a window 314 formed along the first panel 306. The pull tab 312 extends from the first panel 306 over the window 314 so that the tab 312 may be easily identified and gripped by a user.

The envelope 302 is substantially similar to the envelope 202 including a first perforation 324 extending along the first panel 306 on a first side of the tab 312 toward a first edge 310a and a second perforation 328 extending along the first panel 306 on a second side of the tab 312 toward the first edge 310a. The tab 312 extends from the first panel 306 over the window 314 such that when the tray portion 318 extends through the window 314, the tab 312 extends adjacent to the tray portion 318 substantially perpendicularly of the first panel 306. The envelope 302 may also include slits 348 extending from corners 340, 342 toward the first and second perforations 324, 328, respectively, to ensure a clean opening. The tab 312 may be pulled toward the first edge 310a to tear the first panel 306 along the first and second perforations 324, 328 to open the envelope 302 and remove the packet 304 therefrom.

Figure 12:
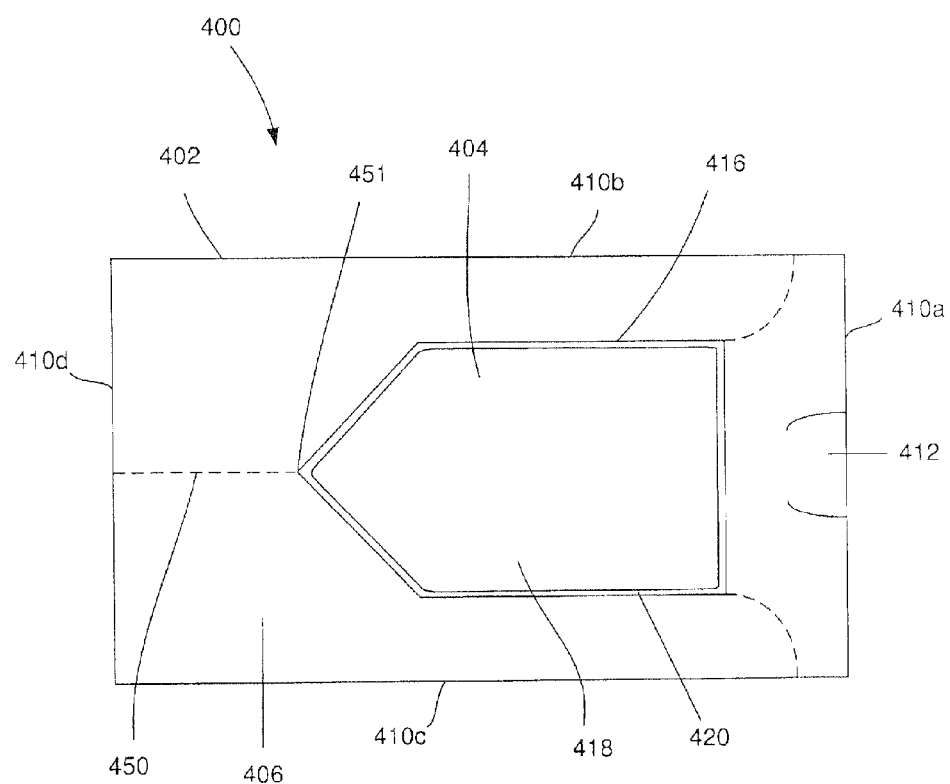
FIG. 12 shows a top plan view of a package according to a still further exemplary embodiment of the present invention.

As shown in FIG. 12, a package 400 according to another exemplary embodiment of the present invention may be substantially similar to the packages 100, 200, 300. The package 400, however, comprises an envelope 402 which further includes a perforation 450. The perforation 450 may extend along a first panel 406 from an edge 410d to a central point 451 of a window 416. In a preferred embodiment, the perforation 450 runs along a straight line. The perforation 450 runs equidistant to edges 410b, 410c from the central point 451 to the middle of the edge 410d.

The perforation 450 allows for easy insertion of a tray portion 418 of a packet 404 into the package 400. In a starting configuration, the perforation 450 is intact. To insert the tray portion 418, the perforation 450 is broken by squeezing together the edges 410b and 410c. In this open configuration, the packet 404 is inserted into the envelope 402 such that a rim 420 is housed within the envelope 402 and the tray portion 418 extends through the window 416. To close the package 400 for transportation, the two portions separated by the perforation 450 are arranged to take substantially the same configuration as in the starting configuration. A label (not shown) is placed across the line defined by the perforation 450. The label is used to hold the two separated portions and to retain the packet 404 in the package 400. In this closed configuration, the envelope 402 may be used to transport the medical device housed therein. As would be understood by the skilled person, the easy inserting perforation can be used with any embodiments 100, 200, 300. The device 400 may further include a pull tab 412 formed substantially similarly to the pull tab 112 and extending over a first edge 410a, as described in greater detail with respect to the device 100.

Figure 13:
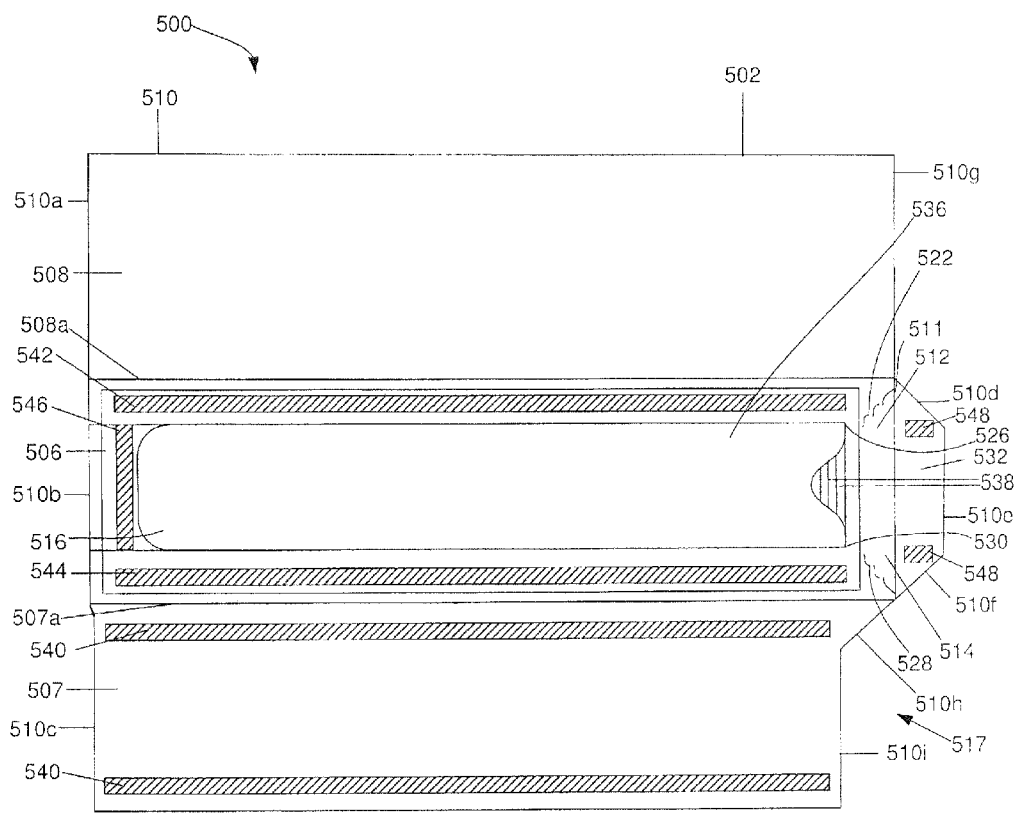
FIG. 13 shows a top plan view of a package according to another exemplary embodiment of the invention in a non-assembled configuration.

FIG. 13 depicts a device 500 according to another embodiment of the invention and formed substantially similarly to the devices 100, 200, 300 except as noted below. The device 500 comprises an envelope 502 which may be opened via a pull tab 512 to access a sealed packet housed therein. Whereas the envelopes 102, 202 and 302 comprise two planar panels connected to one another along an outer edge 310, the envelope 502 is formed of first, second and third planar panels 506, 507, 508 constructed from a single piece of cardboard or heavy paper stock material sized and shaped such that, when folded, the envelope 502 is configured as described below. Specifically, the envelope 502 includes a fold line 507a between the first and second panels 506, 507 and a fold line 508a between the first and third panels 506, 508. In an operative configuration, the packet (not shown) may be easily packed within the envelope 502 by placing the packet along the first panel 506 and folding the second and third panels 507, 508 thereover. Specifically, the second panel 507 may be folded toward the first panel 506 along the fold line 507a. The third panel 508 may then be folded along the fold line 508a so that a portion of the third panel 508 overlaps the second panel 507. One or more adhesive strips 540 may be applied to overlapping portions of the second and third panels 507, 508 to close the envelope 502 and hold the packet 104 therein. Specifically, the adhesive 540 may be applied in two elongated strips disposed on the second panel 507 and extending substantially parallel to the fold line 507a. In an operative configuration, as will be described in greater detail later on, the adhesive 540 on the second panel 507 may lockingly engage the third panel 508 when folded thereover. Although the embodiment of FIG. 13 depicts two elongated adhesive strips 540, any number and arrangement of the adhesive strips 540 may be provided on either the second panel 507 or the third panel 508 without deviating from the scope of the invention. Outer edges 510 of the envelope 505 may be connected and sealed over one another. Specifically, the envelope 502 includes edges 510a, 510b, 510c which may be sealed to one another in the assembled configuration.

The first panel may further comprise a tab 532 extending therefrom having first, second and third edges 510d, 510e, 510f. In an operative configuration, the tab 532 may be folded along a fold line 511, as will be described in greater detail later on. In an exemplary embodiment, a length of the third panel 508 is substantially the same as a length of the first panel 506 so that an edge 510g of the third panel 508 aligns with the fold line 511. The second panel 507 according to this embodiment is shorter than the first and third panels 506, 508. Specifically, the second panel 507 includes a cutout portion 517 configured so that the second panel 507 includes edges 510h and 510i. The edge 510h may be aligned with the edge 510f of the tab 510f while the edge 510i extends substantially parallel to the line 511. As those skilled in the art will understand, the cutout 517 minimizes bulk of the envelope 502 in the region where the tab 532 is folded to maintain a desired degree of flexibility of the assembled envelope 502.

The envelope 502 may also include a window 516 extending through the first panel 506 such that the packet (not shown) and the contents thereof are visible therethrough. The window 516 is formed substantially similarly to the window 216 and includes a transparent film 536 extending thereacross such that the window 516 is covered while permitting the contents of the envelope 502 to be visible therethrough. In an exemplary embodiment, the transparent film 536 may be attached to the first panel 506 via a plurality of adhesive strips 542, 544, 546 or any other suitable known means. Specifically, dimensions of the transparent film 536 are slightly larger than dimensions of the window 516 permitting the adhesive strips 542, 544, 546 to be placed over the areas of overlap where the film 536 extends beyond the edges of the window 516 to permit adhesion of the transparent film 536 to the first panel 506. Specifically, the adhesive strips 542, 544 may extend over an outer periphery of the first panel 506 substantially parallel to the fold lines 507a, 508a and may be spaced from an edge of the window 516 by a distance selected to permit overlap thereof with the transparent film 536. Another adhesive strip 546 may be positioned orthogonal to the adhesive strips 542, 544 and may be substantially parallel to the edge 510b of the first panel 506. In an exemplary embodiment, the window 516 is substantially rectangular although other shapes are envisioned within the scope of the invention.

The pull tab 512 extends over a portion of the window 516 to permit it to be grasped by a user, as described in greater detail earlier. The pull tab 512 may include a plurality of grooves 538 extending therealong and formed substantially similarly to the grooves 238. The grooves 538 provide additional flexibility to the tab 512 and further aid in the gripping thereof by the user. The pull tab 512 is open to a first perforation 522 extending along the first panel 506 from a first corner 526 of the window 516 to the fold line 511 and a second perforation 528 extending along the first panel 506 from a second corner 530 of the window 516 to the fold line 511. The first and second perforations 522, 528 comprise a plurality of arcuate cuts formed through the first panel 506 and arranged in a substantially linear configuration from the window 516 toward the fold line 511. In another embodiment, however, the first and second perforations 522, 528 comprises a plurality of substantially linear cuts. In an operative configuration, the second and third panels 507, 508 are folded over the first panel 506. The tab 532 is then folded about the line 511 to overlap a portion of the third panel 508 and secured thereto using, for example, an adhesive. Specifically, the tab 532 may contain one or more adhesive strips 548 distributed thereover and configured to lockingly engage the third panel 508 when folded thereover. In operation, a user may pull the tab 512 away from the first panel 506 along the first and second perforations 522, 528. Once the first and second perforations 522, 528 have been torn, an opening is formed adjacent the line 511 such that an end of the packet may be grasped and pulled from the envelope 502. Alternatively, instead of using the pull tab 512, a user may choose to lift the tab 532 away from the third panel 508 to provide access to the contents of the envelope 502.

Figure 14:
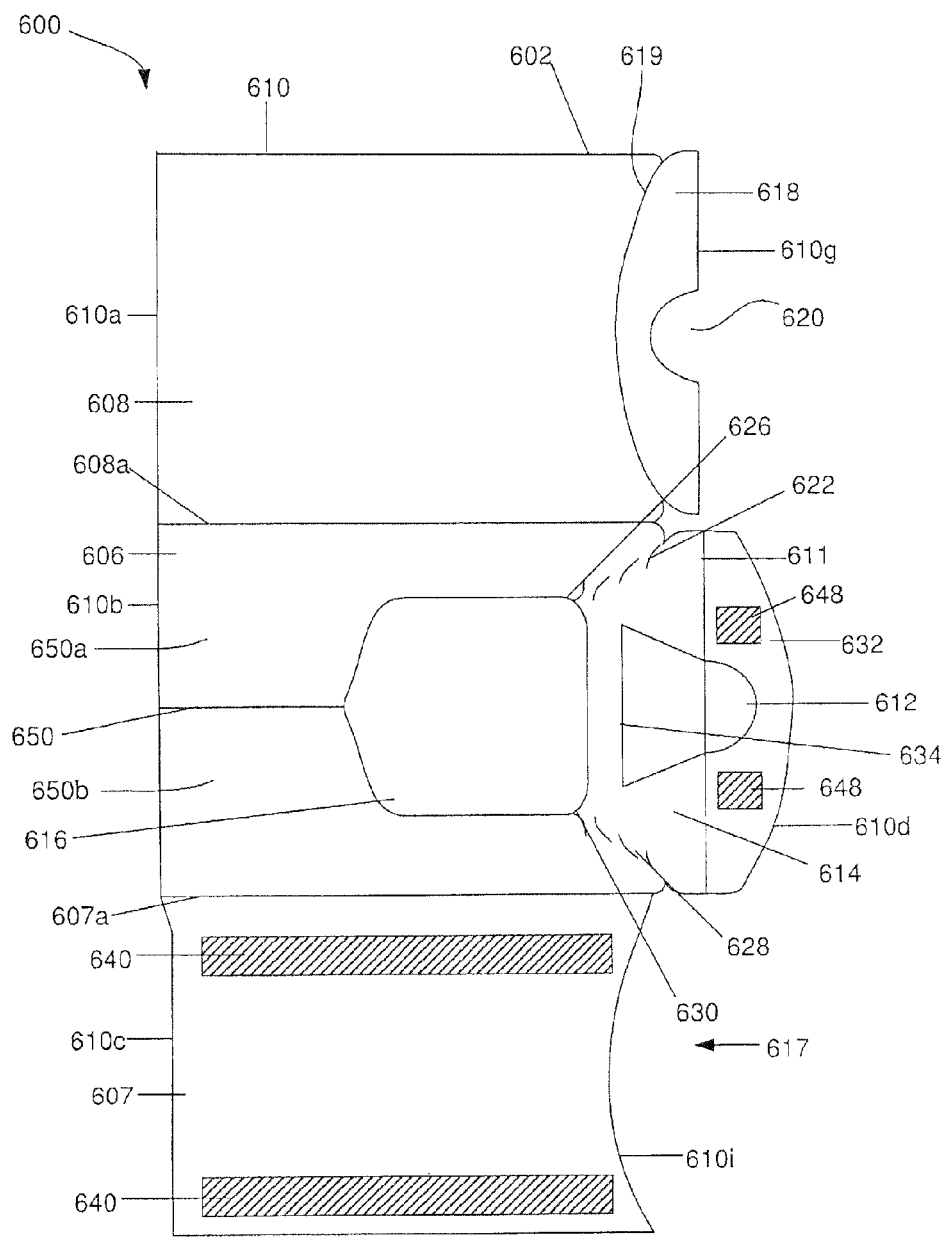
FIG. 14 shows a top plan view of a package according to another exemplary embodiment of the invention in a non-assembled configuration.

FIG. 14 depicts a device 600 according to another embodiment of the invention. The device 600 is formed substantially similarly to the devices 400, 500 except as noted below and includes an envelope 602 formed from a single piece of cardboard or heavy paper stock material sized and shaped such that, when folded, the envelope 602 is configured as described below. The envelope 600 includes first, second and third panels 606, 607, 608 connected to one another at fold lines 607a, 608a. The first, second and third panels 606, 607, 608 are folded to an assembled configuration in substantially the same manner as described above with respect to the envelope 502. Specifically, the second panel 607 is folded about the fold line 607a over the first panel 606. The third panel 608 is then folded about the fold line 608a to overlap the first and second panels 606, 607 and secured thereto, for example, using adhesive strips 640 formed substantially similar to the adhesive strips 540. Edges 610a, 610b, 610c may also be secured to one another as described in greater detail earlier.

The third panel 608 further comprises a third panel tab 618 having an edge 610g opposite the edge 610a. An arcuate fold line 619 is provided between the third panel 608 and the third panel tab 618. A curvature of the arcuate fold line 619 corresponds to a curvature of an edge 610d of the first panel 606. Specifically, as will be described in greater detail with respect to an exemplary assembly technique below, a first panel tab 632 of the first panel 606 is folded inward in a direction toward the first panel 606. A shape and curvature of the first panel tab 632 causes a deflection of the second and third panels 607, 608 away from the first panel 606 to increase a size of a cavity formed within the envelope 602. The third panel tab 618 is then folded over the first panel tab 632 and secured thereto, for example, using adhesive strips 648 formed substantially similar to the adhesive strips 548. As those skilled in the art will understand, this configuration aids in the removal of a packet from the envelope 602, while also reducing stress applied to the packet (not shown) during transport. The second panel 607 may include a cutout 617 defining a substantially arcuate edge 610i corresponding to a shape of the arcuate fold line 619, the cutout 617 reducing bulk of the envelope at the region adjacent a pull tab 612, as described in greater detail with respect to the device 500.

The first panel 606 includes a window 616 formed substantially similarly to the window 416 and having a substantially pentagonal shape, although any other shape is envisioned within the scope of the invention. The first panel 606 further comprises an elongated slit 650 extending from the edge 610b to a central point 651 of the window 616. The slit 650 is formed substantially similarly to the perforation 450 but includes a single elongated slit instead of a plurality of perforations. In a preferred embodiment, the slit 650 runs along a straight line and is substantially equidistant from the fold lines 607a, 608a. The slit 650 allows for easy insertion of, for example, a tray portion of a packet (not shown) into the envelope 602. Specifically, the packet (not shown) may be inserted into the envelope 602 such that a rim of the tray portion (not shown) is housed within the envelope 602 and the tray portion extends through the window 616, as described in greater detail in earlier embodiments. To close the package 600 for transportation, a label (not shown) may be placed across the line defined by the slit 650. The label is used to hold two separated portions 650a, 650b on lateral sides of the slit 650 and to retain the packet within the envelope 602. As those skilled in the art will understand, the slit 650 can be used with any of the devices 100, 200, 300, 400, 500.

The first panel 606 also includes first and second perforations 622, 628 provided adjacent the pull tab 612, the first perforation 622 extending from a first corner 626 of the window 616 to a fold line 611 and the second perforation 628 extending from a second corner 630 of the window 616 to the fold line 611. The tab 612 is formed substantially similarly to the pull tab 112 of the device 100. Specifically, the tab 612 may be defined by a cut 634 extending along a break portion 114 of the envelope 602. The cut 634 extends from the first panel 606 and over the fold line 611 to the panel tab 632 such that the tab 612 may be lifted away from the envelope 602. Thus, the envelope 602 may be opened by grasping the tab 612 and pulling the tab 612 away from the envelope 602 such that the envelope 602 tears along the first and second perforations 622, 628. The first panel tab 632 may have a substantially arcuate edge 610d.

In accordance with an exemplary assembly technique according to the invention, the second and third panels 607, 608 are folded to an overlapping configuration over the first panel 606, and the edges 610a, 610b, 610c are sealed over one another. The first panel tab 632 is then folded inward about the fold line 611 in a direction toward the first panel 606, deflecting the first panel 606 away from the second and third panels 607, 608 to increase a size of a cavity formed therebetween. The third panel tab 618 is then folded about the fold line 619 to overlap the first panel tab 632. The adhesive strips 648 provided over an outer face of the first panel tab 632 lock a position of the first and third panel tabs 632, 628 relative to one another while also sealing the envelop to a closed configuration.

In order to provide access to the contents of the envelope 602, a user may pull the pull tab 612 away from the envelope, tearing the first and second perforations 622, 628. Alternatively, the user may grasp a cutout 620 provided on the third panel tab 618 to pull the third panel tab 618 away from the first panel tab 632. The third and first panel tabs 618, 632 may then be opened in succession to provide access to the contents of the envelope 602.

Figure 15:
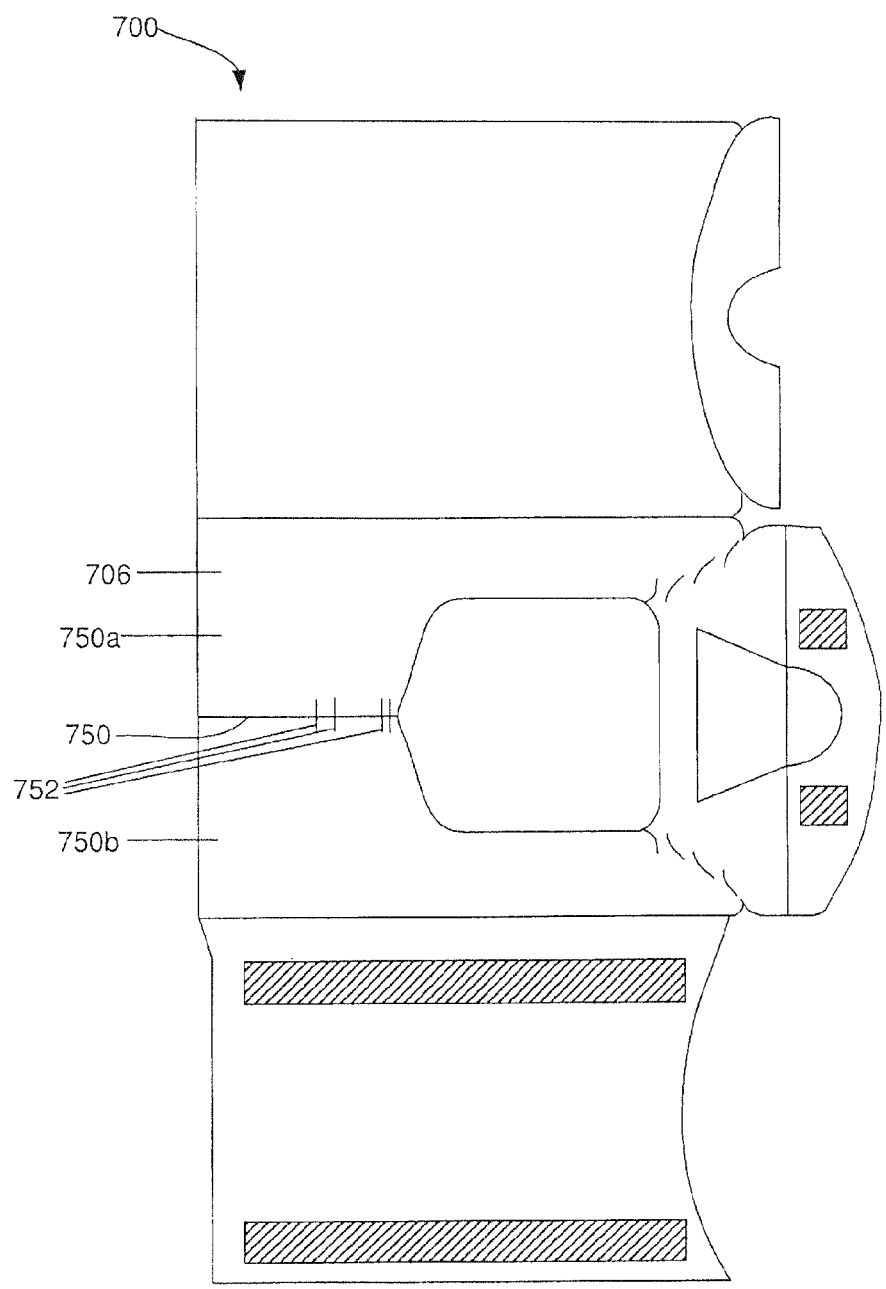
FIG. 15 shows a top plan view of a package according to another exemplary embodiment of the invention in a non-assembled configuration.

FIG. 15 depicts a device 700 formed substantially similarly to the device 600 described above and including a slit 750 formed substantially similar to the slit 650. The device 700 further comprises a plurality of perforations 752 extending substantially perpendicular to the slit 650 and disposed at a plurality of locations along a length thereof. As those skilled in the art will understand, the perforations 752 provide a holding point for attachment of the device 700 to a gluing machine during assembly. It is noted that although the four perforations 752 are depicted, any number and arrangement of the perforations may be used without deviating from the scope of the invention.

Figure 16:
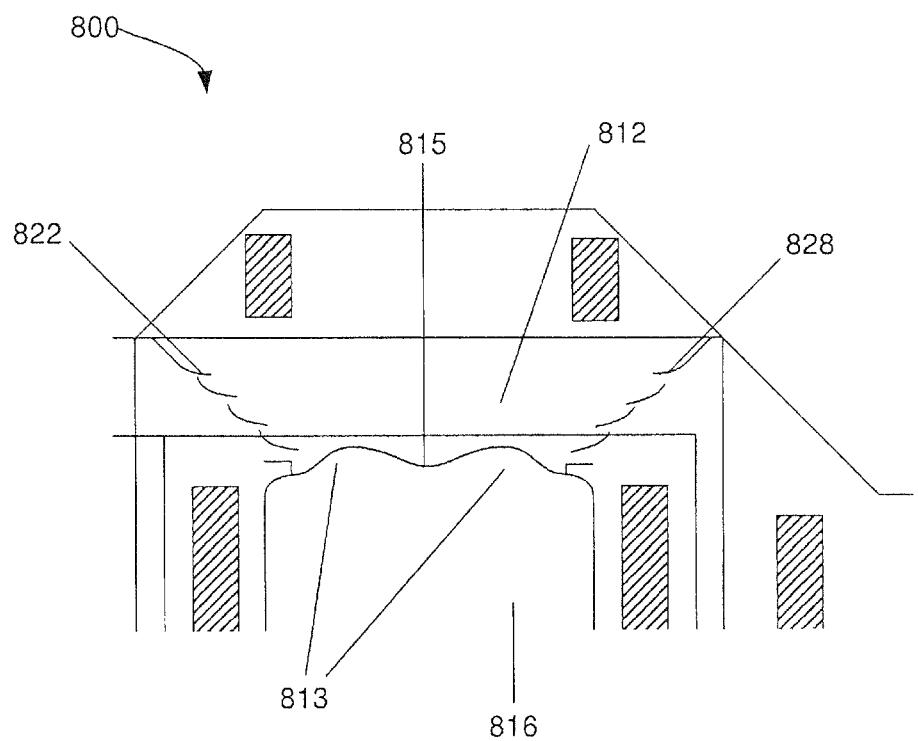
FIG. 16 shows a zoomed top plan view of a package according to another exemplary embodiment of the invention in a non-assembled configuration.

FIG. 16 depicts a device 800 according to another embodiment of the invention. The device 800 may be formed substantially similarly to any of the devices 100-600 described above. However, a pull tab 812 of the device 800 includes first and second concave cutouts 813 defining a convex protrusion 815 extending over a portion of a window 816. The cutouts 813 and protrusion 815 are configured to permit an ergonomic grasping of the pull tab 812 to aid in pulling back of the pull tab 812. Specifically, each of the concave cutouts 813 may be configured and dimensioned to receive a finger of the user to aid in grasping of the pull tab 812.

It will be apparent to those skilled in the art that various modifications and variations can be made in the structure and the methodology of the present invention, without departing from the spirit or scope of the invention. Thus, it is intended that the present invention cover the modifications and variations of this invention provided that they come within the spirit of the appended claims and their equivalents.

What is claimed is:

1. An envelope for housing a medical device, comprising:
   a body including first and second panels connected to one another along a first edge thereof to define an interior space sized and shaped to house a medical device to be sealed within a packet;
   a first opening arrangement including a perforation extending about the body along the first panel to define a break portion breakable from a remaining portion of the body to open the envelope; and
   a second opening arrangement including a tab extending from a portion of the body such that pulling the tab in a direction away from the body opens the envelope, the tab created from a cut extending from the first panel and over the first edge to the second panel such that pulling the tab lifts the tab from the second panel while remaining attached to the first panel.

2. The envelope of claim 1, further comprising a window extending through the first panel, wherein the window is covered by a transparent film extending thereacross and being sized and shaped to accommodate a tray portion of a packet to be housed within the envelope, wherein a first portion of the perforation extending along the first panel extends from the window to the first edge of the body.

3. The envelope of claim 2, wherein a portion of the tab overlaps a portion of the window, the tab including a concave groove aiding grasping thereof.

4. The envelope of claim 1, wherein the first opening arrangement extends across the first and second panels.

5. The envelope of claim 1, further comprising a third opening arrangement including a perforation extending centrally into the body along one of the first and second panels to define a portion breakable by squeezing, the perforation including one of a single elongated slit extending into the body and a plurality of elongated slits intersecting one another.

6. The envelope of claim 5, further comprising a label arrangeable to close the body across the perforation of the third opening arrangement.

7. The envelope of claim 2, wherein the body includes a third panel connected to the first panel along a second edge thereof to define the interior space sized and shaped to house the medical device to be sealed within the packet.

8. The envelope of claim 7, wherein a second portion of the perforation extending along the first panel extends from the window to the second edge of the body.

9. The envelope of claim 7, wherein the tab extends from the first panel and is attached to the third panel.

10. An envelope for housing a medical device, comprising:
    a body including first and second panels connected to one another along an edge thereof to define an interior space sized and shaped to house a medical device to be sealed within a packet;
    a first opening arrangement including a tab extending from a portion of the body such that pulling the tab in a direction away from the body opens the envelope, the tab created from a cut extending from the first panel and over the first edge to the second panel such that pulling the tab lifts the tab from the second panel while remaining attached to the first panel; and
    a second opening arrangement including a perforation extending centrally into the body along one of the first and second panels to define a portion breakable by squeezing.

11. An envelope for housing a medical device, comprising:
    a body including first and second panels connected to one another along an edge thereof to define an interior space sized and shaped to house a medical device sealed within a packet;
    an opening arrangement including a perforation extending centrally into the body along one of the first and second panels to define a portion breakable by squeezing; and
    a label arrangeable to close the body across the perforation.

* * * * *